United States Patent [19]
Bienhaus et al.

[11] Patent Number: 5,855,852
[45] Date of Patent: *Jan. 5, 1999

[54] VESSEL FOR REDUCING CONTAMINATION IN THE TREATMENT OF LIQUIDS

[75] Inventors: Gerhard Bienhaus, Wielenbach; Michael Fritz, Biblis; Jürgen Schwab, Ketsch; Edda Geisler, Mannheim; Herbert Harttig, Altrip; Heinz Macho, Fürth, all of Germany

[73] Assignee: Boehringer Mannheim GmbH, Mannheim, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 623,798

[22] Filed: Mar. 29, 1996

[30] Foreign Application Priority Data

Apr. 1, 1995 [DE] Germany ........................ 295 05 652 U

[51] Int. Cl.$^6$ ........................................ B01L 3/00
[52] U.S. Cl. .................... 422/102; 422/100; 422/101; 422/102; 422/103; 422/104; 436/180
[58] Field of Search ................... 422/100, 101, 422/102, 103, 104; 436/180

[56] References Cited

U.S. PATENT DOCUMENTS

| | | | |
|---|---|---|---|
| 3,586,064 | 6/1971 | Brown | 422/101 X |
| 3,601,152 | 8/1971 | Kenworthy | 137/525 |
| 3,682,596 | 8/1972 | Stone | 422/101 |
| 3,706,305 | 12/1972 | Berger et al. | 128/2 |
| 3,799,426 | 3/1974 | Pates et al. | 229/44 |
| 4,192,919 | 3/1980 | Raghavachari | 435/292 |
| 4,376,391 | 3/1983 | Brunnee | 73/863.12 |
| 4,533,643 | 8/1985 | Bell et al. | 436/178 |
| 4,644,807 | 2/1987 | Mar | 73/864.62 |
| 4,760,939 | 8/1988 | Ball et al. | 222/23 |
| 4,900,515 | 2/1990 | Miramanda | 422/100 |
| 4,956,298 | 9/1990 | Diekmann | 430/311 |
| 5,003,988 | 4/1991 | Guirguis | 128/771 |
| 5,139,742 | 8/1992 | Heijink | 422/58 |
| 5,160,704 | 11/1992 | Schluter | 422/101 |
| 5,178,838 | 1/1993 | Sala et al. | 422/102 |
| 5,221,483 | 6/1993 | Glenn et al. | 210/641 |
| 5,387,334 | 2/1995 | Kuroda et al. | 210/121 |

FOREIGN PATENT DOCUMENTS

| | | |
|---|---|---|
| 0 182 370 | 11/1984 | European Pat. Off. . |
| 0 561 003 | 9/1993 | European Pat. Off. . |
| 1 541 115 | 6/1969 | Germany . |
| 23 28 718 | 1/1975 | Germany . |
| 24 42 149 | 3/1976 | Germany . |
| 31 39 702 | 4/1983 | Germany . |
| 36 39 949 | 6/1988 | Germany . |
| 40 21 355 | 4/1991 | Germany . |
| 40 20 442 | 1/1992 | Germany . |
| 41 24 577 | 1/1992 | Germany . |
| 42 04 554 | 7/1993 | Germany . |
| 42 14 634 | 7/1993 | Germany . |
| 44 09 842 | 10/1994 | Germany . |
| 44 12 286 | 10/1995 | Germany . |
| 58-67339 | 4/1983 | Japan . |

OTHER PUBLICATIONS

Leonard et al, Amicon, *Accelerated Restriction Mapping and Cloning with Ultrafiltration*, pp. 2–8.

Qiagen News, For Biochemisrty and Molecular Biology, *High Performance Sequencing Templates–Introducing QIAwell–8 System*, Issue No. 1/94, pp. 1–20.

Qiagen News, For Biochemistry and Molecular Biology, *mRNA without Intermediate Total RNA Preparation*, Issue No. 2/94, pp. 1–16.

*Primary Examiner*—Harold Y. Pyon
*Attorney, Agent, or Firm*—Nikaido, Marmelstein, Murray & Oram LLP

[57] ABSTRACT

A vessel for reducing contamination of liquids is formed of a vessel body with an inlet opening and an outlet opening therein. A closing device is attached to the vessel body adjacent the outlet opening. The closing device closes the outlet opening, and includes a normally closed one-way valve which is openable by a predetermined pressure from within the vessel body.

27 Claims, 3 Drawing Sheets

VESSEL FOR REDUCING CONTAMINATION IN THE TREATMENT OF LIQUIDS

BACKGROUND OF THE INVENTION

Subject matter of the invention is a vessel for reducing contamination in the treatment of liquids, said vessel having an inlet and an outlet opening; the latter opening can be closed in a special way.

In many fields of application, the treatment of liquids requires particular care with respect to actively avoiding contamination which could adversely affect the environment. This applies particularly to noxious liquids, but also to liquids which are used or generated in the analysis of components. The treatment steps to prepare a sample liquid for an analysis are usually carried out in the same laboratory or even the same room as the analysis itself. The use of aerosols, for example, often leads to heavy contamination of the environment with sample components; this in turn interferes with the analysis of components of other samples. An erroneous result can have terrible consequences for the patient, especially when analyzing components in the field of medical and clinical diagnostics.

Analyses that are based on the detection of nucleic acids in a sample have recently been introduced as diagnostic tools owing to their relatively high specificity. These tests are a considerable technical challenge since the contents of nucleic acids and especially the nucleic acids to be detected is a very small one while nucleic acids having similar sequences and other components which may interfere with the determination are also present in the same sample. Experience has shown that amplification procedures which have recently become more and more popular are used to produce a multitude of identical nucleic acids dependent on the presence of certain nucleic acid sequences to be tested; this greatly improves the sensitivity of the test, allowing to even detect individual nucleic acids. The risk involved in the possible high sensitivity of the tests is that contamination of other samples even with only one single nucleic acid from the environment can cause, i.e. simulate, a positive result. When using nucleic acid tests, it is therefore necessary to avoid in a particularly effective manner already the generation of contamination, i.e. the release of nucleic acids from a sample or a reaction mixture into the environment.

When preparing samples for the analysis of components, especially nucleic acids, methods have recently been used where the sample liquid and the components to be analyzed contained therein are subject to a treatment in the vessel wherein liquid is introduced into the vessel through an inlet opening and removed again through an outlet opening after undergoing one or several treatment steps. Such vessels are commercially available in the form of columns containing materials for the separation of components from the liquid, an example being the QIAamp Kit manufactured by Qiagen. These vessels are contained in another vessel, so that liquid which may leak is released into this second vessel and not into the environment. This kind of liquid treatment is, however, complex and requires a corresponding second vessel. Moreover, these vessels are used in the centrifuges in order to transfer the liquid into the second vessel.

DE-A-4020442 describes a system wherein a rigid seal which seals the surface of blood sample vessels is pierced open with the aid of device that is equipped with a needle. Said needle can be covered by a protective cap. A separate tool is, hence, necessary to open and close the vessel.

DE-A-4124577 describes a reagent bottle whose bottom side is closed with a screw cap.

U.S. Pat. No. 3,706,305 describes a container where liquids can be transported with the aid of needles which pierce a membrane.

U.S. Pat. No. 3,601,152 discloses a valve where an elastic piece is completely removed from a projection. Said projection has no lateral openings.

The use of such a valve to avoid contamination has not yet been described.

DE-C-4214634 describes a pipetting aid to absorb liquids, said aid comprises an elastic hollow body and several valves for the in- and outlet of air.

DE-C-4204554 describes an ampoule for liquids where an inlet opening is opened by piercing a plastic membrane using a tip that is integrated in a funnel. The removal of liquid cannot be accomplished by applying pressure differences DE-A-3139702 describes a vessel for handling paste-like sample material. The outlet openings are closed by means of snap-tops.

U.S. Pat. No. 4,956,298 describes a separation or reaction column that can be emptied via centrifugation. The outlet opening is closed with the aid of a snap-top that has to be mechanically removed.

U.S. Pat. No. 3,799,426 describes a container which is provided with a projection at its top; said projection prevents the vessel from falling through an apertured plate.

EP-A-0 561 003 describes a vessel for receiving liquids wherein the liquid is passed through several membranes when entering the vessel. An elastic seal of the outlet opening is not proposed.

EP-A-0 182 370 describes a blood storage device having a blood intake tube; said blood intake tube can be tightly sealed with a cap that is placed on the tube. An opening with the aid of pressure differences is not proposed.

U.S. Pat. No. 5,139,742 describes a device which comprises two pieces that can be brought into a position to allow the passage of liquid. The outlet opening in this element is not elastically closed with the aid of another element. The opening of the liquid passage is not accomplished with the aid of pressure differences.

DE-A-4021355 describes a blood removal device that is closed with the aid of a pierceable elastic plate. The device is opened with the aid of a hollow needle. However, the closure is provided to allow liquid to be taken into the device. To accomplish this, a vacuum is generated via another opening.

DE-A-2442149 describes a vessel for removing blood followed by a centrifugation procedure where the outlet opening is closed with the aid of a stopper. In order to open the outlet opening, the stopper must be manually removed.

DE-A-2328718 describes a disposable syringe where a screw cap is used to close an outlet opening.

DE-A-1541115 describes a disposable syringe where a semi-spherical cap is used to close the inlet opening.

U.S. Pat. No. 5,003,988 describes an apparatus for the detection of biological substances where liquid is pressed through a cylindrical opening.

DE-a-3639949 describes a method of separating long-chain nucleic acids with the aid of a filter material where the sample is made to pass through this filter material. The device used is a cartridge that is not opened by applying pressure.

U.S. Pat. No. 5,221,483 describes a device for filtering liquids wherein the liquid is passed through a porous filter and/or membranes. Inlet or outlet openings are not opened by applying pressure.

Leonhardt et al. (Amicon Biosolutions, 4/1994, pp 2–7) describe a system for the ultra-filtration of liquids wherein the liquid is transported across a filter by means of centrifugation.

Quiagen News, No. 1/94, pp 1–20, describe a system where liquids can be drawn through vessels. The outlet openings of these vessels can, however, not be reversibly opened or closed. Said literature reference also describes a vessel for cleaning nucleic acids wherein the liquid is passed through a filter material by means of centrifugation. Again, the outlet opening is not opened by applying pressure.

The latter vessel is also described in Quiagen News 2/94, pp 1–14.

It was, hence an object of the present invention to improve currently known methods for treating liquids by providing a new vessel.

SUMMARY OF THE INVENTION

Subject matter of the invention is a vessel for reducing contamination in the treatment of liquids; said vessel has an inlet and an outlet opening. The latter opening can be closed with the aid of an element which elastically exerts pressure against the outlet opening and can be reversibly opened by applying low or access pressure.

The vessel of the present invention can principally have any desired shape. Generally, it has an interior that is sufficiently large to receive the desired amount of liquid. In order to accomplish this, the vessel can have an inner form (A17) and an outer form (A19). The inner and outer shapes can principally be selected as desired. It is, however, preferred that the inner form in the area where the liquid is received is as smooth as possible; also, the area where contact is made with the liquid should have no or only few recesses or projections where remaining liquid could be retained. Hollow cylindrical vessels with an inlet opening (A10) at one end and an outlet opening (A11) at the other end, are particularly preferred with respect to both use and manufacture.

Vessels that are preferably used for analytical purposes have a preferred length between 100 and 5 mm, preferably approx. 50 mm, and an inner diameter between 2 and 20 mm, preferably approx. 8 mm.

In accordance with the invention, the vessel is tapered in the area of its outlet opening such that the diameter at the outlet opening is substantially smaller than the diameter of the remaining vessel The invention proposes that this outlet opening be closed with the aid of an element (A12) which elastically exerts pressure against the outlet opening (A11) (auto-sealing). The element itself can be made of an elastic material which exerts pressure against the opening, e.g. rubber or silicone, or be connected with an elastic material which presses said element against the opening, e.g. a spring or also another rubber material. The necessary force is preferably applied perpendicularly and permanently against the opening. Owing to said contact pressure exerted against the opening and the edge surrounding said opening, the closure of the invention is distinguished from other closures. Numerous of the closures used as valves on other instruments can be used in accordance with the invention. Another preferred feature of the closure is that it can be opened by applying a low pressure to the side facing away from the interior of the vessel. In order to achieve this, a gap through which liquid can emerge from the interior of the vessel through an outlet opening toward the outside, is opened between the elastic material and the edge of the outlet opening. In order to open the valve and transport liquid from the vessel through the outlet opening, it has proven to be expedient to select a pressure difference between 0.4 and 0.6 bar such that the higher pressure is applied inside the vessel while the lower pressure is applied outside the vessel. This is accomplished either by applying pressure inside the vessel (preferred) or by applying a vacuum outside the vessel (especially in the area of the outlet opening).

DETAILED DESCRIPTION

Figure 1:
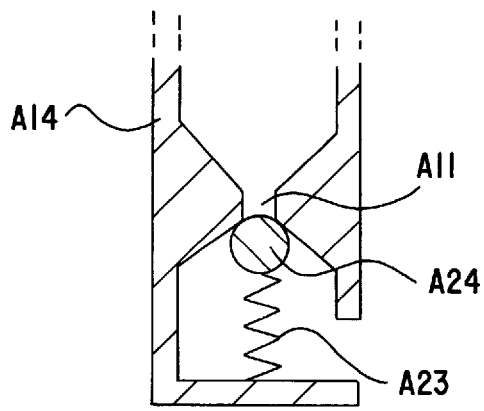
FIG. 1 illustrates a first embodiment of the invention.

The following is a description of a few embodiments of closures with reference to the drawing.

FIG. 1 shows a ball valve. A spiral spring (A23) permanently presses a sphere (A24) against a tapered outlet opening. Said sphere (A24) is made of metal, e.g. steel or plastic (e.g. nylon) and can also have an elastic coat. The force of the spring is set such exceeds the force exerted on the outlet opening as a consequence of the gravitational force exerted by the liquid in the glass, and also the force that acts on the outlet opening during possible treatment steps, e.g. insertion of a suitable structural form through the liquid present in the glass. Said force should, however, not be substantially greater as this may render difficult the opening of the valve by applying a low pressure.

Figure 2:
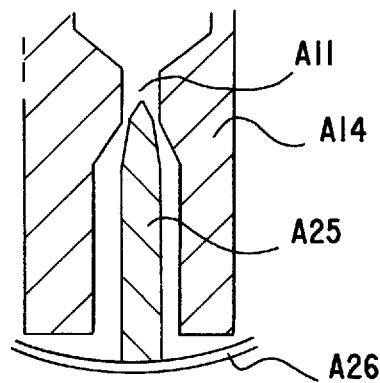
FIG. 2 illustrates a second embodiment of the invention.

FIG. 2 shows a needle valve. A leave spring (A26) or a rubber band press a needle (A25) which seals the outlet opening from the bottom against said outlet opening. The outlet opening is configured as a passage in an outlet projection (A14).

Figure 3:
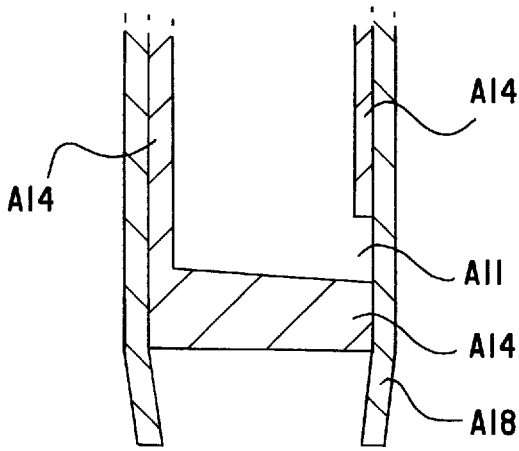
FIG. 3 illustrates a third embodiment of the invention.

FIG. 3 is a preferred embodiment of a closure in the form of a tubular valve. A thin-walled rubber tube is pulled over an outlet (A14) having a lateral outlet opening (A11); said tube tightly urges against the outer walls of the outlet such that there is no space left between the edge and the outlet opening where liquid could escape. Possible materials are in particular natural rubber or silicon rubber. The tube preferably extends beyond the edges of the outlet opening. This also reduces the atomization of liquid.

As compared to other designs, the valve does not tend to jam the outlet opening. The valve is distinguished in that it acts largely neutral with respect to viscosity in a range between 1 and 100 mPas both in its function and in its efficiency. With this type of valve, the flow-through per time unit can be adjusted and controlled via pressure parameters.

Figure 4:
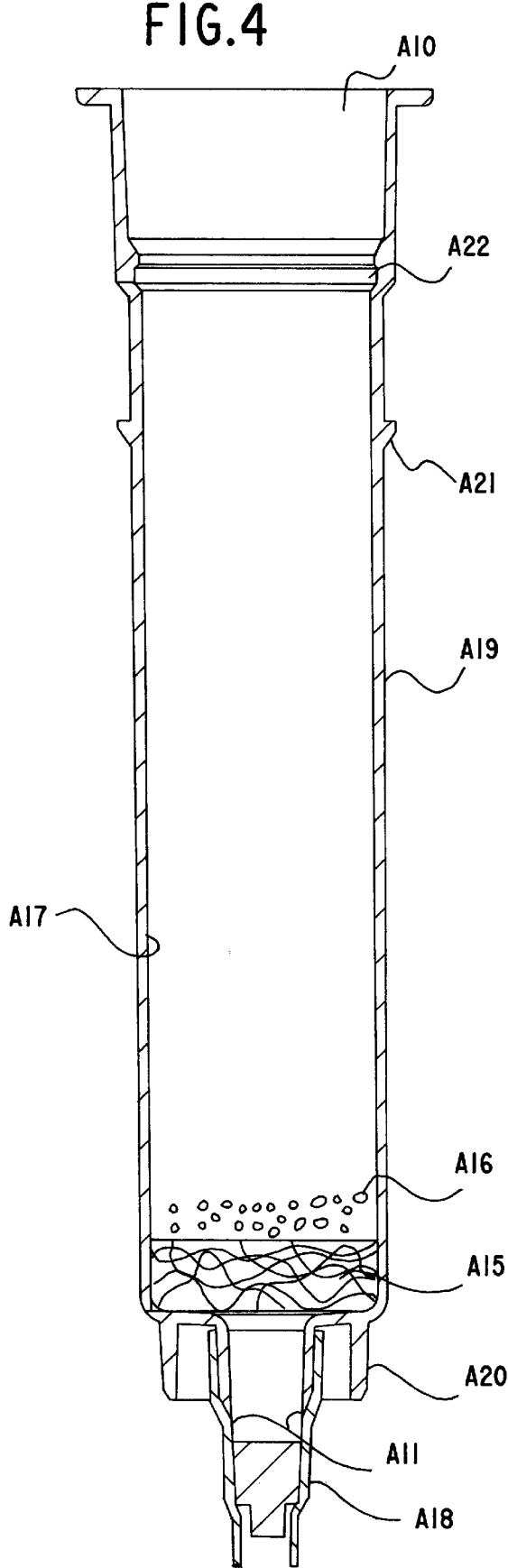
FIG. 4 illustrates a vessel according to the present invention.

FIG. 4 shows a vessel in accordance with the invention with a tube valve where provision is made for two outlet openings on opposite side walls. The representation shows a longitudinal section of the outlet openings. Tube (A18) act as an element which covers the outlet piece such that the outlet openings (A11) are covered. Additional preferred features are shown in the upper part of the shown vessel. The outer wall (A19) of the vessel has circumferential projections (A21) which serve to hold the vessel in a holding plate that has holes which are slightly larger than the diameter of the vessel. In the area of the inlet opening (A10), the inner form is slightly enlarged so as to receive a lid B which is placed in the inside to completely close the vessel. Moreover, a circumferential notch (A22) can be seen to hold additionally desired structural forms in the vessel.

Figure 5:
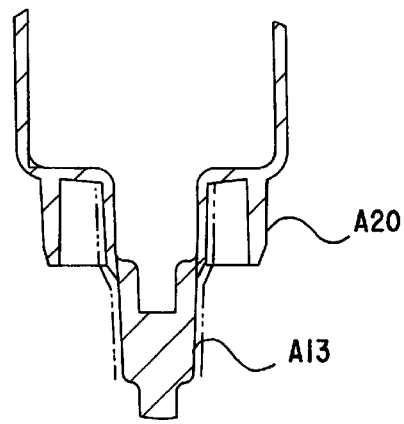
FIG. 5 illustrates a closure for the vessel of FIG. 4.

FIG. 5 shows the closure of FIG. 4 without a section through the outlet openings. This representation shows another preferred feature of the tubular valve, namely the tapered outer form of the outlet element facing away from the vessel. This ensures on the one hand good positioning of the tube on the outlet piece and also prevents the escape of liquid indirection toward the vessel when the valve is opened as a consequence of the increased pressure in the upper part. Moreover, the tapered portion reduces the atomizing effect and, hence, the formation of aerosols. The tube (as is indicated) exceeds past the lower end of the outlet piece. Another expedient feature, i.e. a circumferential bar (A20) can also be clearly seen. This bar can be used to connect a vessel with another instrument in order to apply a low pressure from the outside to the valve. It, hence matches the form of a reception area on the instrument side, seals the vessel/instrument interface with the aid of an 0-ring, and secures the vessel against undesired removal from the instrument bores.

Figure 6:
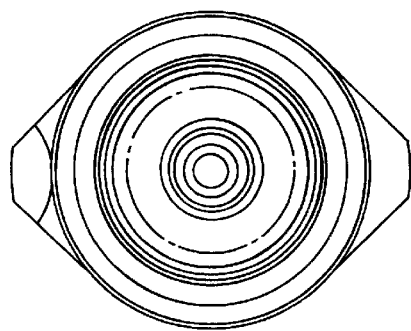
FIG. 6 illustrates a top view of a vessel according to FIG. 4.

FIG. 6 is a top view of a vessel in accordance with the invention according to FIG. 4. It also shows a general feature which is the possible option of attaching lateral connecting elements at the upper end of the vessel; this allows to freely take and insert the vessel lid with the aid of a handle to thus avoid contamination caused by handling.

Figure 7:
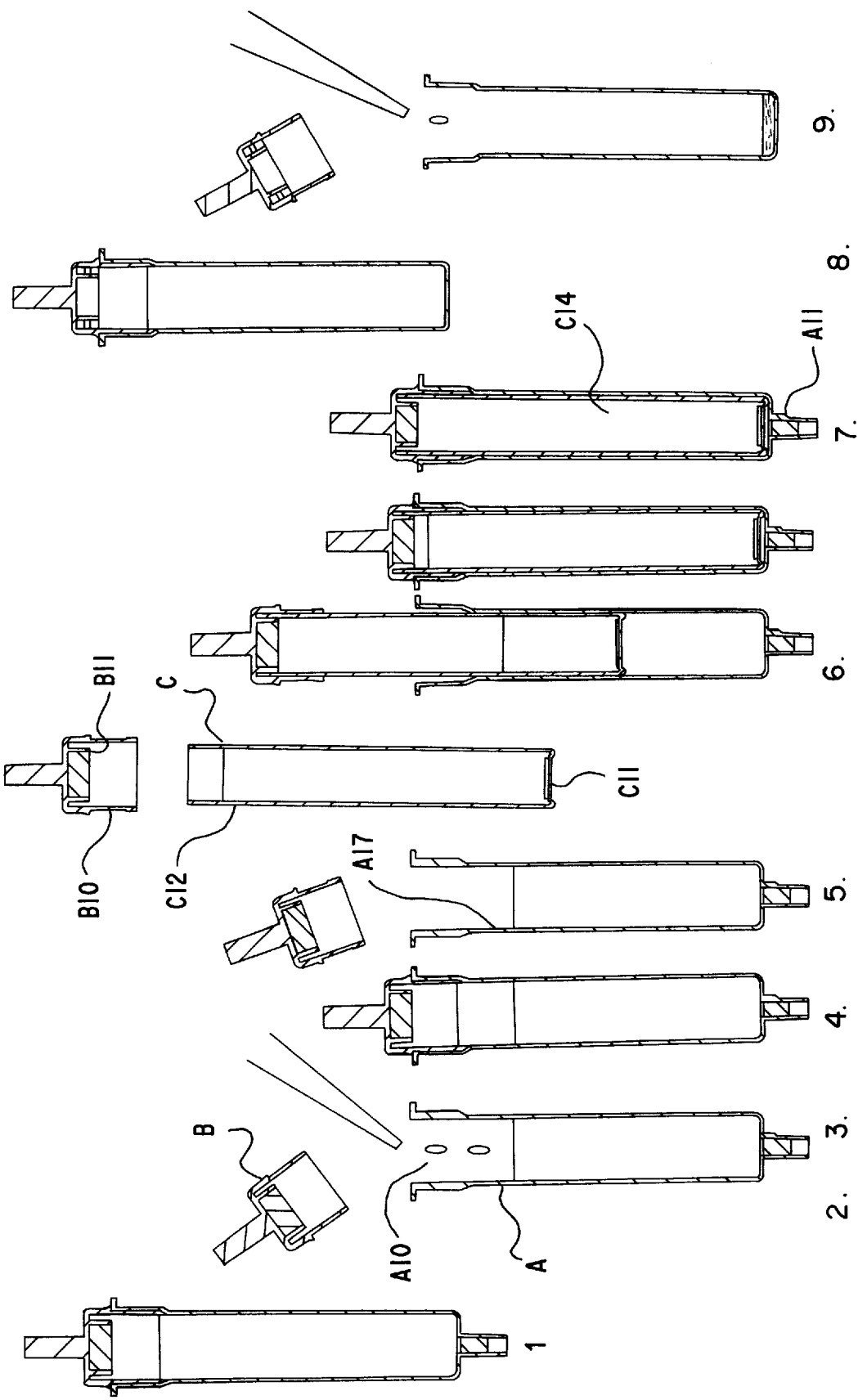
FIG. 7 illustrates a top view of a vessel according to the present invention.

FIG. 7 shows the operating flow of Example 2. The vessel in accordance with the invention may also comprise additional elements and functional elements that may be necessary to satisfy the desired function. If, for example, the vessel is intended to remove particle-type objects from a liquid, e.g. cells, a filter material (A15, not shown in FIG. 7) may be provided between inlet and outlet opening which allows liquid to pass, but not cells.

Another possibility for removing components, e.g. dissolved substances, such as antigens, cells or nucleic acids, from a liquid is to incorporate an absorbing material (A16, also not shown in FIG. 7) to which the components may bind. The absorber material can be retained in the vessel either by means of a filter or, if magnetic particles are used, by providing a magnet.

The outer form of the vessel is preferably slightly tapered toward the bottom. When the vessel is placed into the recess of a heating block to carry out heating or cooling procedures, which requires a tight fit with the outer form of the vessel to support heat transfer, it is thus possible to remove the vessel from the heating block even after several temperature cycles.

The thickness of the walls in the area of the hollow cylinder is preferably configured such that it allows good heat transfer from the outside to the liquid in the vessel and only a minor interference with possibly used magnetic fields. The material of the vessel is selected such that it is form-stable and the temperature range between 4° and 100° C. Suitable materials are plastics such as polypropylene as they satisfy the above mentioned demands and are also easy to manufacture by means of injection molding.

The self-sealing outlet opening prevents a reflux of liquid back into the reaction chamber. Contamination of the sample with waste material is thus excluded. This is particularly critical when a (minor) low pressure is to be applied in the reaction chamber (e.g. to remove the aforementioned structural form from the vessel).

The vessel in accordance with the invention is extraordinarily well suited for reducing contamination in the treatment of liquids. To achieve this, the lid is removed, liquid is filled in, reagents are added if necessary, incubation for a given time period is carried out (with the lid closed if desired) and subsequently liquid is drawn off toward the outside through an outlet opening by applying a low pressure which opens the valve. The liquid can either be used gain or in case components remained in the vessel, the liquid is discarded and the vessel is further treated to obtain the components bound therein.

With the vessel in accordance with the invention it is possible to carry out all desired chemical and biological reactions.

This includes in particular methods of analyzing components of sample liquids, or methods of isolating components from sample liquids. Reaction steps which can be carried out with this method are in particular the immobilization (binding) of components to a solid matrix, the separation of liquid from components, treatment of immobilized components such as the lysis of immobilized cells, washing steps or modification of immobilized components, e.g. by labeling with a detectable group.

The vessel of the invention can be advantageously used for the sample preparation in the analysis of nucleic acids.

Another subject matter of the invention is, hence, a method of isolating a component from a sample by
  filling the sample into a vessel via an inlet opening (A10),
  adding a matrix to immobilize the component,
  incubating under conditions suitable for the immobilization, and
  removing the liquid through an outlet opening (A11), while said outlet opening is sealed by an element which elastically exerts pressure against the outlet opening and can be reversibly opened by applying low pressure or excess pressure.

The method of the invention and the vessel are particularly well suited for the automated treatment of liquids.
the following examples explain the invention in greater detail:

EXAMPLE 1

The embodiment of the vessel in accordance with the invention has an overall length of 45.3 mm, an outer diameter of 8.8 mm, and an inner diameter of 6.95 mm. The tube has three functional areas.

The first, top area, the inlet, is configured such that the vessel can be sealed with respect to the environment with the aid of sealing lips of a corresponding lid and positioning said lid on vessel edge (A10). In the interior of the inlet opening area, an annular notch (A22) is provided at the inner wall to allow a structural form to snap in. The inlet opening has an overall length of 6.1 mm, an outer diameter of 8.8 mm, an inner diameter of 6.95 mm. The notch at the interior of the tube is 6.15 mm away from the edge (1) measured toward the bottom. The circumferential notch has a depth of 0.10 mm and a height of 0.5 mm.

The second area of the vessel is a hollow cylindrical tube with a length of 32.4 mm, an outer diameter (A19) of 7.8 mm, and an inner diameter of 6.95 mm. In this area, provision is made for holding elements (A21) for positioning in an apertured plate.

The third, bottom area, the outlet opening, has the form of a truncated cone (d1=2.8 mm, d2=2.1 mm, h=6.8 mm) with a cylindrical tapered portion, an outer diameter of 1 mm and a height of 1 mm. In its interior, the outlet is configured such that liquid can be transported out of the vessel if necessary via a vertical inner channel (d=1.5 mm, h=3.8 mm) and two horizontal outlet openings (A11) (d=1.0 mm, h=1.0 mm). Said openings are sealed with the aid of a highly flexible plastic tube (A18) (made of Silastik manufactured by Reichelt Chemietechnik; inner diameter=2.0 mm, wall thickness= 2.4 mm). By applying a defined low pressure or excess pressure, the outlet opening is opened toward the bottom, and liquid is allowed to escape without atomization. The outlet opening in the form of a truncated cone has a circumferential bar (A20) with a height of 2.5 mm, a wall thickness of 3.5 mm, and a radius of 1.65 mm. Its outer geometry is configured such that it is suitable to receive and release a vessel in a corresponding block of the instrument which also holds the device for absorbing liquid.

EXAMPLE 2

In a particular embodiment for the preparation of nucleic acid-containing sample solutions, the working steps shown in FIG. 7 are carried out. In a first step, the vessel (1.), which is closed with a lid (B), is opened (2.); the cell-containing sample liquid is pipetted into the sample vessel (A) of the invention through an inlet opening (A10); the vessel is closed and incubated with a material (4.) to which the cells are bound in order to obtain nucleic acids. To accomplish this, the material can either exhibit specific binding properties for binding the surface of the cells, e.g. by immobilization of antibodies to the surface antigens, or an absorber material (A16); however, it is also possible to provide a material with filtering properties (A15) to retain the cells when liquid passes through said material, e.g. when removing such liquid from the vessel. Conditions for immobilizing cells at surfaces are known to the expert, e.g. from Methods in Enzymology Vol. 171, Biomembranes/Part R Transport Theory: Cell and Model Membranes, Edited by Sidney Fleischer, Becca Fleischer, Department of Molecular Biology, Vanderbilt University, Nashville, Tenn.

In another step, the liquid is removed from the sample vessel while cells whose nucleic acids are to be isolated remain in the vessel where they are bound to the material. If the cell binding material is a particle-type material, the cells can be retained in that material is magnetic, and a magnetic field is applied to the sample vessel from the outside; said field has to be strong enough to retain the particle-type material in the sample vessel when the liquid is removed. If the outlet opening is located in the lower part of the sample vessel and below the retained cells, the liquid can be drawn off by applying a minor vacuum.

In order to remove other potentially interfering sample components from the cells, it is also possible to provide one or several washing steps. To achieve this, washing liquid is filled into the sample vessel; said washing liquid dissolves possible contamination which, however, does not essentially affect the binding of the cells to the surface of the cell-binding material. Such washing solutions are known to the expert, e.g. from cell separation protocols or corresponding cleaning kit protocols for nucleic acids. They basically depend on how the cells bind to the material.

After the last washing solution has been removed from the sample vessel (A), the purified, enriched cells are brought into contact with a suitable lysis liquid to release the nucleic acids from the cells. The reagents of this lysis solution largely depend on the type of immobilized cells. If the cells are bacteria, the lysis solution preferably contains proteinase K to digest the cell walls. Optionally, the lysis can be supported by heating or cooling and agitating the reaction mixture. If magnetic particles are used as cell-binding material, the mixing can also be accomplished with the aid of a magnet. Moreover, it is possible to mix the solution by shaking the sample vessel. Once digestion is completed, the nucleic acids to be isolated are freely accessible in the solution.

Even during lysis, it is preferred that the reaction vessel be closed by a lid in order to avoid contamination from the environment. After completion of the lysis, the lid is removed, preferably with the aid of a corresponding mechanical device. Subsequently, a structural form (C), whose outer contour (C12) matches the inner contour (A17) of the sample vessel, is introduced into the sample vessel which contains a mixture of digestion products of the cells and the nucleic acids. This structural form is hollow and sealed toward the sample vessel and toward the reaction mixture by means of a filter. The introduction of the structural form (C) is preferably accomplished with the aid of an element (B11) of lid (B) which also contains an element (B10) suitable to close the sample vessel. In this case, the structural form is taken up with the aid of a lid (II) and introduced in the sample vessel while the latter is closed. During this procedure, the reaction mixture can enter the hollow space (C14) of the structural form across filter (C11) (IV). By providing a filter, it is possible to prevent large particles from entering into the hollow space; if the filter already has nucleic acid binding properties, the nucleic acid can already be bound to the filter while the reaction mixture is passing through. In this case, it is expedient to select a glass fiber containing filter material.

In the next step, the remaining lysis reaction mixture is removed from the device consisting of A and C, e.g. by drawing off solution from the sample vessel through an outlet opening (A11) located in the lower portion of the vessel. The solution that has entered the hollow body (C14) of the structural form is, hence, also removed so that the filter more or less no longer contains any liquid.

The nucleic acids bound to the filter can now be removed therefrom; this can be accomplished either in the sample vessel or after removal therefrom (8.) by contacting (9.) with the solution of a nucleic acid-desorbing substance (e.g. a low concentration salt solution) and be subject to further treatment (analysis, modification, amplification, etc.).

We claim:

1. A vessel for reducing contamination of liquids contained therein, said vessel comprising:

a vessel body having an inlet opening and an outlet opening therein;

closing means attached to said vessel body adjacent said outlet opening, for closing said outlet opening, said closing means comprising a self-sealing normally closed one-way valve which includes a biasing means which biases said valve in a closing direction toward said outlet opening, said closing means being openable by a predetermined pressure differential between an inside and an outside of the vessel body.

2. A vessel as recited in claim 1, wherein said closing means comprises an elastic material which sealingly engages the outlet opening.

3. A vessel as recited in claim 1, wherein said closing means comprises an outlet piece having a side wall, said side wall being tapered toward an outside thereof.

4. A vessel as recited in claim 1, said vessel including a filter disposed between said inlet opening and said outlet opening.

5. A vessel as recited in claim 1, further comprising an adsorber material disposed between said inlet opening and said outlet opening.

6. A vessel as recited in claim 1, further comprising a lid configured to open and close said inlet opening.

7. A vessel as recited in claim 1, wherein said vessel body includes attaching means for attaching said vessel to a holding means, which holds the vessel therein.

8. A vessel as recited in claim 1, further comprising an alignment notch on an inner surface of said vessel body, said alignment notch for engaging structural form members therein.

9. A vessel as recited in claim 1, wherein said predetermined pressure differential is provided by applying a vacuum to the outside of the vessel body.

10. A vessel as recited in claim 1, wherein said pressure differential is provided by applying a predetermined pressure to the inside of the vessel body.

11. A vessel as recited in claim 1, wherein said vessel body comprises a first portion having a first inner diameter, and a second portion having a second inner diameter less than said first inner diameter, wherein said outlet opening is formed in said second portion, and wherein said closing means engages an outer perimeter of the second portion forming said outlet opening.

12. A vessel as recited in claim 1, wherein said one way valve comprises a ball and spring.

13. A vessel as recited in claim 1, wherein said normally closed one-way valve comprises a needle valve which is springably urged in a closing direction toward said outlet opening.

14. A vessel for reducing contamination of liquids contained therein, said vessel comprising:

a vessel body having an inlet opening and an outlet opening therein; and closing means attached to said vessel body adjacent said outlet opening, for closing said outlet opening, said closing means comprising a normally closed one-way valve, said closing means being openable by a predetermined pressure differential between an inside and an outside of the vessel body, wherein said closing means comprises a tubular valve and wherein the tubular valve comprises a tube which covers an outlet opening and extends past the outlet opening, said tube forming a flexible closing member which flexes to allow liquid to escape from said outlet opening.

15. A vessel as recited in claim 14, wherein said closing member comprises a tube covering the outlet opening.

16. A vessel as recited in claim 14, wherein an inner cross section of the vessel body is cylindrical.

17. A vessel as recited in claim 14, further comprising an annular ring coupled to said closing means.

18. A vessel as recited in claim 14, wherein said vessel body comprises a hollow cylinder.

19. A vessel as recited in claim 18, wherein said vessel body comprises a hollow cylinder having a conical outer form which is tapered toward the outlet opening.

20. A method of isolating a component from a sample, said method comprising the steps of:

filling a vessel with the sample through an inlet opening of said vessel;

adding a matrix to the vessel, said matrix being selected to allow immobilization of the component;

incubating the sample and the matrix under selected conditions thereby immobilizing the component; and removing the sample through an outlet opening of the vessel, said outlet opening being closed by a closing means which elastically biases a closing element against the outlet opening, and which can be opened by a pressure differential between an inside and an outside of said vessel.

21. A method as recited in claim 20, wherein said pressure differential is provided by applying a vacuum to the outside of the vessel.

22. A method as recited in claim 20, wherein said pressure differential is provided by applying a predetermined pressure to the inside of the vessel.

23. A vessel for reducing contamination of liquids contained therein, said vessel comprising:

a vessel body having an inlet opening and an outlet opening therein;

closing means attached to said vessel body adjacent said outlet opening, for closing said outlet opening, said closing means comprising a closing element for closing said opening, and a spring means for springably urging said closing element toward said opening in a closing direction.

24. A vessel as recited in claim 23, wherein said closing element comprises a sphere, and wherein said spring means comprises a coil spring which springably urges said sphere against a perimeter of said outlet opening.

25. A vessel as recited in claim 23, wherein said spring means comprises a leaf spring which urges said closing element against an outer perimeter of said outlet opening.

26. A vessel as recited in claim 23, wherein said spring means comprises a rubber band which springably urges said closing element against an outer perimeter of the opening.

27. A vessel as recited in claim 23, wherein said vessel body comprises a first portion having a first inner diameter, and a second portion having a second inner diameter less than said first inner diameter, wherein said outlet opening is formed in said second portion, and wherein said closing means engages an outer perimeter of the second portion forming said outlet opening.

* * * * *